United States Patent [19]

Khcheyan et al.

[11] 3,980,728

[45] Sept. 14, 1976

[54] METHOD OF CO-PRODUCING ISOPRENE AND 2-METHYL-1-BUTENE

[76] Inventors: Khachik Egorovich Khcheyan, Prospekt Mira, 118-a, kv. 190; Olga Mikhailovna Revenko, B.Pirogovskaya 29/31, kv. 107; Margarita Petrovna Tikhonova, ulitsa Grekova, 18, korpus 3, kv. 120, all of Moscow, U.S.S.R.

[22] Filed: Aug. 25, 1975

[21] Appl. No.: 607,812

Related U.S. Application Data

[63] Continuation of Ser. No. 383,458, July 27, 1973, abandoned.

[52] U.S. Cl. ................... 260/680 R; 260/683 R
[51] Int. Cl.² ............................................ C07C 3/00
[58] Field of Search ................... 260/680 R, 683 R

[56] References Cited
UNITED STATES PATENTS

| | | |
|---|---|---|
| 2,275,232 | 3/1942 | Rice .................................. 260/683 |
| 3,396,208 | 8/1968 | Scott ................................. 260/683 |

FOREIGN PATENTS OR APPLICATIONS

| | | |
|---|---|---|
| 432,430 | 7/1935 | United Kingdom ................ 260/683 |

*Primary Examiner*—Oscar R. Vertiz
*Assistant Examiner*—Brian E. Hearn
*Attorney, Agent, or Firm*—Haseltine, Lake & Waters

[57] ABSTRACT

Isobutylene is reacted with alkanes having from 1 to 3 carbon atoms at 600°–800°C in the presence of an initiating agent, viz., oxygen alone or air, taken in an amount of 1 to 20 vol.% of the initial reaction mixture (as oxygen). The proposed method is simple to carry out from technological viewpoint, is based upon the readily available and inexpensive original stock and makes it possible to obtain the end products at high yields. Under optimum conditions of the realization of the proposed process the isobutylene conversion percentage is as high as 28 to 50, the total yield of the end products reaching 70 to 100 percent by weight as referred to the reacted isobutylene.

6 Claims, No Drawings

METHOD OF CO-PRODUCING ISOPRENE AND 2-METHYL-1-BUTENE

This application is a continuation application of Ser. No. 383,458, filed July 27, 1973, now abandoned.

The present invention relates to a method of co-producing isoprene and 2-methyl-1-butene. Said products are extensively applicable in industrial organic-synthesis practice. Isoprene is largely used for producing synthetic rubbers; it acquires special importance in connection with the now-developing production the regular-structure (cis-1,4-polyisoprene) isoprene rubber which by its structure and properties is most proximal to natural rubber. 2-methyl-1-butene is the semi-product of organic synthesis and is used particularly in the synthesis of isoprene.

An industrial process is known for derivation of isoprene by dehydrogenating $C_5$ hydrocarbons (an isopentane-isopentene fraction) which occurs in a single- or double-step.

Said process suffers from a decided disadvantage, viz., limited sources of isopentane-isopentene fraction; besides, the process of dehydrogenation occurs with a low selectivity and is accompanied by the formation of large amounts of byproducts, viz., piperylene and acetylene (as it is known commonly, piperylene has not so far found any industrial application whatever). Moreover, said process offers considerable difficulties with respect to the isolation and purification of the end-product.

A currently used process is an industrial two-stage process for isoprene production, residing in the interaction of isobutylene and formaldehyde with the formation of 4,4'-dimethyldioxane-1,3, followed by splitting the resultant product into isoprene in the presence of a calcium phosphate catalyst.

The afore-discussed process is accompanied by the formation of a large proportion of byproducts, up to 0.4 t per ton of isoprene. Besides, formaldehyde used in said process and derived by the catalytic oxidation of methane, is a relatively expensive product.

It is an object of the present invention to provide a process for co-producing isoprene and 2-methyl-1-butene which would be simple from a technological viewpoint.

It is another object of the present invention to provide a process which would be based upon a readily available and inexpensive starting stock.

It is one more object of the present invention to provide a process enabling the production of high-yield end products.

In keeping with said and other objects the invention resides in that isobutylene is made to react with alkanes having from 1 to 3 carbon atoms at 600°–800°C in the presence of an initiating agent, viz., oxygen or air taken in an amount of 1 to 20 vol.% of the initial reaction mixture (as oxygen).

The proposed process is simple from a technological viewpoint, i.e., the end products are synthesized in a single stage; it enables the production of high-yield end products viz., with the isobutylene conversion percentage within 28 to 50 and the total yield of the end products (i.e., isoprene and isoamylene-I) reaches 70 to 100 percent as referred to the reacted isobutylene. The cardinal advantage of the proposed process is its economy, inasmuch as it is based upon an inexpensive and readily available raw stock (i.e., isobutylene and the alkanes having from 1 to 3 carbon atoms). Thus, isobutylene used in the proposed process can be isolated in large proportions from the fraction of the $C_4$ hydrocarbons that results from the cracking or pyrolysis of petroleum, or from isobutane dehydrogenation.

Most preferable among the alkanes is methane which is a naturally occurring gas.

The interaction of isobutylene and the alkane is expediently in a molar ratio from 1:3 to 1:8, respectively.

It is recommended that the initiating agent be used in an amount of from 5 to 15 vol.% of the initial reaction mixture (as oxygen).

To attain maximum isobutylene conversion percentage it is recommended that the isobutylene and alkane interaction occur at a feed space velocity equal to 6000–10000 hr$^{-1}$.

To render the process more selective and improve heat withdrawal conditions, it is expedient that the isobutylene-alkane interaction occur in the presence of an inert diluent, such as nitrogen or steam.

A mixture of isobutylene, alkane and initiating agent is passed through a reaction vessel at 600°–800°C, preferably at 675°–725°C and at various space velocities, preferably at 6000 to 10000 hr$^{-1}$. The alkanes used may be methane, ethane, propane or mixtures thereof, but preferably methane. The molar ratio of isobutylene to alkane in the initial reaction mixture may vary within a wide range, but the optimum isobutylene-alkane molar ratio ranges within 1:3 to 1:8, respectively. As an initiating agent use is made of oxygen itself or air, the concentration of said agent in the initial reaction mixture being 1 to 20 vol.% (in terms of oxygen), preferably 5 to 15 vol.%. As has been stated hereinbefore, it is recommended that the isobutylene-alkane interaction occur in the presence of an inert diluent, such as nitrogen, argon, carbon dioxide or steam.

End products resultant from the interaction of isobutylene and the alkane, are isolated from reaction mixture by the known conventional methods, such as rectification. Inasmuch as 2-methyl-1-butene is readily dehydrogenated into isoprene, it may be returned into the process for the purpose, or subjected to dehydrogenation in a separate apparatus.

The byproduct of the herein-discussed process, viz., propylene finds its most extensive application in the chemical industry.

Thus, the principal advantage of the proposed process resides in that it enables the production of such a valuable monomer as isoprene based upon the readily available and inexpensive raw stock, viz., isobutylene which is a resultant product of petroleum refining processes, and methane which is either a naturally occurring gas or a petroleum refining product. The proposed process is simple from a technological viewpoint and provides a high yield of the end products.

For better understanding of the present invention a number of examples of co-producing isoprene and 2-methyl-1-butene are given below.

EXAMPLE 1

A mixture of isobutylene, methane and oxygen taken in a molar ratio of 1:5.4:0.78 (the oxygen volume percentage in the mixture being 10.92) was passed through a quartz reaction vessel having an inside diameter of 22 mm and the reaction zone 100 mm long, at a space velocity equal 7928 hr$^{-1}$ and a temperature of 700°C.

With the process proceeding under said conditions the isobutylene conversion percentage was 45.3, the total yield of isoprene and 2-methyl-1-butene was 71 percent by weight as referred to the reacted isobutylene, the weight ratio of isoprene to 2-methyl-1-butene was equal to 1:1.87 and the propylene yield was 37.7 percent by weight as referred to the reacted isobutylene.

EXAMPLE 2

A mixture of isobutylene, methane and oxygen taken in a molar ratio of 1:6.5:0.65 (the oxygen volume percentage in the mixture being 8) was passed through the reaction vessel described in Example 1 at a space velocity equal to 6334 $hr^{-1}$ and a temperature of 700°C.

With the process occurring under said conditions the isobutylene conversion percentage was 26.9, the total isoprene and 2-methyl-1-butene yield was 90.5 percent by weight as referred to the reacted isobutylene, the isoprene-to-2-methyl-1-butene weight ratio was equal to 1:6 and the propylene yield was 19.7 percent by weight as referred to the reacted isobutylene.

EXAMPLE 3

A mixture of isobutylene, methane and oxygen in a molar ratio of 1:8:0.47 (the oxygen content in the mixture being 5 percent by volume) was passed through the reaction vessel described in Example 1, at a space velocity of 7127 $hr^{-1}$ and a temperature of 675°C.

With the process occurring under said conditions the isobutylene conversion percentage was 5.6, the total isoprene and 2-methyl-1-butene yield was 122 percent by weight, the isoprene-to-2-methyl-1-butene weight ratio was equal to 1:2.9 and the propylene yield was 0.22 percent by weight as referred to the reacted isobutylene.

EXAMPLE 4

A mixture of isobutylene, methane and oxygen in a molar ratio of 1:8:1.58 (the oxygen content in the mixture being 14.98 percent by volume) was passed through the reactor at a space velocity of 7514 $hr^{-1}$ and a temperature of 725°C.

With the process occurring under said conditions the isobutylene conversion percentage was 46.7, the total isoprene and 2-methyl-1-butene yield was 66.6 percent by weight as referred to the reacted isobutylene, the isoprene-to-2-methyl-1-butene weight ratio was equal to 1:2.4 and the propylene yield was 34.6 percent by weight as referred to the reacted isobutylene.

EXAMPLE 5

A mixture of isobutylene, methane and oxygen at a molar ratio of 1:2.8:0.33 (the oxygen content in the mixture being 8 percent by volume) was passed through the reactor of Example 1 at a space velocity of 6212 $hr^{-1}$ and a temperature of 681°C.

With the process conducted under said conditions the isobutylene conversion percentage was 16.45, the total yield of isoprene and isoamylene was 70 percent by weight as referred to the reacted isobutylene, the isoprene-to-2-methyl-1-butene weight ratio was equal to 1:6.2 and the propylene yield was 32.4 percent by weight as referred to the reacted isobutylene.

EXAMPLE 6

A mixture of isobutylene, propane and oxygen in a molar ratio of 1:6.5:0.65 (the oxygen content in the mixture being 8 percent by volume) was passed through the reaction vessel of Example 1 at a space velocity of 6300 $hr^{-1}$ and a temperature of 700°C.

With the process occurring under such conditions the isobutylene conversion percentage was 33.3, the total yield of isoprene and 2-methyl-1-butene was 63.5 percent by weight as referred to the reacted isobutylene, the isoprene-to-2-methyl-1-butene weight ratio was 1:1.4 and the propylene yield was 36.8 percent by weight as referred to the reacted isobutylene.

EXAMPLE 7

A mixture of isobutylene, methane and oxygen in a molar ratio of 1:5.4:0.75 (the oxygen content in the mixture being 10.5 percent by volume) was passed through the reaction vessel of Example 1 at a space velocity of 10700 $hr^{-1}$ and a temperature of 704°C.

With the process occurring under said conditions the isobutylene conversion percentage was 19, the total yield of isoprene and 2-methyl-1-butene was 63.5 percent by weight as referred to the reacted isobutylene, the isoprene-to-2-methyl-1-butene weight ratio was 1:2.2 and the propylene yield was 35.5 percent by weight as referred to the reacted isobutylene.

EXAMPLE 8

A mixture of isobutylene, methane and oxygen in a molar ratio of 1:5.4:0.065 (the oxygen content therein being 1 percent by volume) was passed through the reaction vessel of Example 1 at a space velocity of 7500 $hr^{-1}$ and a temperature of 700°C.

With the process occurring under such conditions the isobutylene conversion percentage was 3, the total yield of isoprene and 2-methyl-1-butene was 95.7 percent by weight as referred to the reacted isobutylene, the isoprene-to-2-methyl-1-butene weight ratio was 1:7.7 and the propylene yield was 16.6 percent by weight in terms of the reacted isobutylene.

EXAMPLE 9

A mixture of isobutylene, methane and oxygen in a molar ratio of 1:5.4:1.6 (the oxygen content therein being 20 percent by volume) was passed through the reaction vessel of Example 1 at a space velocity of 10850 $hr^{-1}$ and a temperature of 700°C.

With the process proceeding under said conditions the isobutylene conversion percentage was 60, the total yield of isoprene and 2-methyl-1-butene was 49 percent by weight in terms of the reacted isobutylene, the isoprene-to-2-methyl-1-butene weight ratio was 1:3.2 and the propylene yield was 37.6 percent by weight in terms of the reacted isobutylene.

EXAMPLE 10

A mixture of isobutylene, methane and oxygen in a molar ratio of 1:1:0.1 (the oxygen content therein being 5 percent by volume) was passed through the reaction vessel of Example 1 at a space velocity of 9300 $hr^{-1}$ and a temperature of 680°C.

With the process occurring under such conditions the isobutylene conversion percentage was 40.32, the total yield of isoprene and 2-methyl-1-butene was 49 percent by weight in terms of the reacted isobutylene, the isoprene-to-2-methyl-1-butene weight ratio was 1:2.2 and the propylene yield was 30 percent by weight in terms of the reacted isobutylene.

EXAMPLE 11

A mixture of isobutylene, methane and oxygen in a molar ratio of 1:15:1.18 (the oxygen content therein being 5 percent by volume) was passed through the reaction vessel of Example 1 at a space velocity of 21500 hr$^{-1}$ and a temperature of 780°C.

With the process running under such conditions the isobutylene conversion percentage was 46.5, the total yield of isoprene and 2-methyl-1-butene was 50 percent by weight in terms of the reacted isobutylene, the isoprene-to-2-methyl-1-butene weight ratio was 1:0.84 and the propylene yield was 35 percent by weight in terms of the reacted isobutylene.

EXAMPLE 12

A mixture of isobutylene, methane and air in a molar ratio of 1:2.4:3.6 (the oxygen content therein being 11.5 percent by volume) was passed through the reaction vessel of Example 1 at a space velocity of 7900 hr$^{-1}$ and a temperature of 700°C.

With the process carried into effect under said conditions the isobutylene conversion percentage was 27.15, the total yield of isoprene and 2-methyl-1-butene was 54 percent by weight in terms of the reacted isobutylene, the isoprene-to-2-methyl-1-butene weight ratio was 1:2.7 and the propylene yield was 35.5 percent by weight in terms of the reacted isobutylene.

EXAMPLE 13

A mixture of isobutylene, methane, oxygen and steam in a molar ratio of 1:2:0.45:1 (the oxygen content therein being 10 percent by volume) was passed through the reaction vessel of Example 1 at a space velocity of 6800 hr$^{-1}$ and a temperature of 712°C.

With the process occurring under such conditions the isobutylene conversion percentage was 42, the total yield of isoprene and 2-methyl-1-butene was 42 percent by weight in terms of the reacted isobutylene, the isoprene-to-2-methyl-1-butene weight ratio was 1:3.1 and the propylene yield was 38 percent by weight in terms of the reacted isobutylene.

EXAMPLE 14

A mixture of isobutylene, methane and oxygen in a molar ratio of 1:8:0.5 (the oxygen content therein being 5 percent by volume) was passed through the reaction vessel of Example 1 at a space velocity of 1840 hr$^{-1}$ and a temperature of 725°C.

With the process conducted under said conditions the isobutylene conversion percentage was 12, the total yield of isoprene and 2-methyl-1-butene was 64.3 percent by weight in terms of the reacted isobutylene, the isoprene-to-2-methyl-1-butene weight ratio was 1:4.25 and the propylene yield was 36.5 percent by weight in terms of the reacted isobutylene.

EXAMPLE 15

A mixture of isobutylene, methane and oxygen in a molar ratio of 1:3:0.44 (the oxygen content therein being 10 percent by volume) was passed through the reaction vessel of Example 1 at a space velocity of 10300 hr$^{-1}$ and a temperature of 635°C.

With the process occurring under said conditions the isobutylene conversion percentage was 22.4, the total yield of isoprene and isoamylene was 65.5 percent by weight in terms of the reacted isobutylene, the isoprene-to-2-methyl-1-butene weight ratio was 1:2.2 and the propylene yield was 35.2 percent by weight in terms of the reacted isobutylene.

EXAMPLE 16

A mixture of isobutylene, methane, oxygen and nitrogen in a molar ratio of 1:2.4:0.77:2.9 (the oxygen content therein being 11.5 percent by volume) was passed through the reaction vessel of Example 1 at a space velocity of 7900 hr$^{-1}$ and a temperature of 700°C.

With the process proceeding under such conditions the isobutylene conversion percentage was 27.15, the total yield of isoprene and 2-methyl-1-butene was 66 percent by weight in terms of the reacted isobutylene, the isoprene-to-2-methyl-1-butene weight ratio was 1:1.75 and the propylene yield was 32.5 percent by weight in terms of the reacted isobutylene.

EXAMPLE 17

A mixture of isobutylene, ethane and oxygen in a molar ratio of 1:6.5:0.65 (the oxygen content therein being 8 percent by volume) was passed through the reaction vessel of Example 1 at a space velocity of 6000 hr$^{-1}$ and a temperature of 690°C.

With the process occurring under said conditions the isobutylene conversion percentage was 33, the total yield of isoprene and 2-methyl-1-butene was 63 percent by weight in terms of the reacted isobutylene, the isoprene-to-2-methyl-1-butene weight ratio was 1:1.4, the propylene yield was 37 percent by weight in terms of the reacted isobutylene.

What is claimed is:

1. A method of co-producing isoprene and 2-methyl-1-butene, comprising reacting isobutylene with an alkane having from 1 to 3 carbon atoms at 600° to 800°C in the presence of an initiating agent which is oxygen alone or in the form of air, taken in an amount of 1 to 20 percent by volume of the initial reaction mixture calculated as oxygen wherein the isobutylene to alkane molar ratio is from 1:1 to 1:15.

2. A method as claimed in claim 1, wherein said alkane use is methane.

3. A method as claimed in claim 1, wherein the isobutylene is reacted with the alkane at a molar ratio thereof from 1:3 to 1:8, respectively.

4. A method as claimed in claim 1, wherein the initiating agent is taken in an amount of 5 to 15 percent by volume of the initial reaction mixture calculated as oxygen.

5. A method as claimed in claim 1, wherein the isobutylene is reacted with the alkane at a space velocity from 6000 to 10000 hr$^{-1}$.

6. A method as claimed in claim 1, wherein the isobutylene is reacted with the alkane in the presence of an inert diluent selected from the group consisting of nitrogen and steam.

* * * * *